United States Patent
Dam

(10) Patent No.: US 7,661,293 B2
(45) Date of Patent: Feb. 16, 2010

(54) ULTRASONIC SYSTEM FOR DETECTING AND QUANTIFYING OF AIR BUBBLES/PARTICLES IN A FLOWING LIQUID

(75) Inventor: Naim Dam, Muttontown, NY (US)

(73) Assignees: Cosense, Inc., Hauppauge, NY (US); Fresenius Medical Care Holdings, Inc., Waltham, MA (US)

( * ) Notice: Subject to any disclaimer, the term of this patent is extended or adjusted under 35 U.S.C. 154(b) by 305 days.

(21) Appl. No.: 11/703,025

(22) Filed: Feb. 6, 2007

(65) Prior Publication Data

US 2008/0184784 A1    Aug. 7, 2008

(51) Int. Cl.
  G01N 29/032    (2006.01)
  G01N 29/02     (2006.01)
  G01N 29/024    (2006.01)

(52) U.S. Cl. .................. 73/19.03; 73/61.75; 73/597; 73/598

(58) Field of Classification Search .......... 73/19.03, 73/61.75
See application file for complete search history.

(56) References Cited

U.S. PATENT DOCUMENTS

| | | | | |
|---|---|---|---|---|
| 3,921,622 | A * | 11/1975 | Cole | 600/437 |
| 4,068,521 | A * | 1/1978 | Cosentino et al. | 73/19.03 |
| 4,341,116 | A * | 7/1982 | Bilstad et al. | 73/290 V |
| 4,730,493 | A * | 3/1988 | Lebaud et al. | 73/599 |
| 5,392,638 | A * | 2/1995 | Kawahara | 73/61.49 |
| 5,394,732 | A * | 3/1995 | Johnson et al. | 73/19.1 |
| 6,142,008 | A | 11/2000 | Cole et al. | |
| 6,515,487 | B1 * | 2/2003 | Dawson et al. | 324/639 |
| 6,622,542 | B2 * | 9/2003 | Derek et al. | 73/19.03 |
| 6,796,195 | B2 | 9/2004 | Povey et al. | |
| 7,047,809 | B2 | 5/2006 | Cobb | |
| 2009/0078047 | A1 * | 3/2009 | Dam | 73/606 |

FOREIGN PATENT DOCUMENTS

| | | | |
|---|---|---|---|
| EP | 446605 A1 * | 9/1991 |
| JP | 04158258 A * | 6/1992 |
| JP | 09178712 A * | 7/1997 |
| JP | 2002-333434 A | 11/2002 |
| JP | 2003-043017 A | 2/2003 |
| KR | 10-2003-0035584 A | 5/2003 |
| WO | WO 01/92867 A1 * | 12/2001 |

* cited by examiner

Primary Examiner—Herzon Williams
Assistant Examiner—Rose M Miller
(74) Attorney, Agent, or Firm—Gordon D. Coplein

(57) ABSTRACT

A system using ultrasonic energy for detecting and quantifying air bubbles and/or particles in a liquid flowing in a tube by a non-invasive and non-destructive technique has an ultrasonic sensor having piezoelectric transmitter and receiver elements placed opposing on the outside of the tube wall and energy in the ultrasonic frequency range is transmitted from the transmitter element to the receiver element. The received ultrasonic energy is amplified and detected and preferably split into a steady state (DC) component and a varying or transient (AC) component respectively indicative of the absence and the presence of an air bubble or a particle in the liquid. The two components of the signal are applied to an A/D converter whose output is supplied to a microprocessor which uses the digital data that corresponds to the presence of the varying transient component to indicate the presence of an air bubble and/or a particle and to measure its characteristics. The presence of the steady-state component indicates that the system is operating properly to providing a continuous self check against any system malfunction.

10 Claims, 3 Drawing Sheets

FIGURE: 1

ULTRASONIC SYSTEM FOR DETECTING AND QUANTIFYING OF AIR BUBBLES/PARTICLES IN A FLOWING LIQUID

FIELD OF THE INVENTION

The present invention is directed to a system using ultrasonic energy for detecting and quantifying air bubbles and/or particles in a liquid stream.

BACKGROUND OF THE INVENTION

Medical and industrial developments have created a growing need for detecting and analyzing air bubble and/or particles in a flowing liquid. Industrial applications include products such as engine oil and hydraulic fluids where particle contamination can deteriorate performance. In the medical field, detection of air emboli in blood during kidney dialysis or heart-lung transplant surgery is a function that is necessary to accomplish.

Accordingly, a need exists to provide a system that is able to detect air bubbles and/or particles present in a liquid stream. It is also desirable that such a system be as simple and inexpensive as possible.

BRIEF DESCRIPTION OF THE INVENTION

The present invention is directed to a novel system that uses ultrasonic energy for detecting and quantifying air bubbles and/or particles in a liquid flowing in a tube by a non-invasive and non-destructive technique. In accordance with the invention, an ultrasonic sensor is placed on the outside of the wall of a tube in which a liquid is flowing. The sensor has piezoelectric transmitter and receiver elements. Energy in the ultrasonic frequency range is supplied to the transmitter element which transmits the ultrasonic energy through the tube wall and the liquid flowing in the tube to the receiver element. The signal from the sensing element is amplified and detected, preferably by a full wave detector. It includes a steady state (DC) and a varying or transient (AC) component, the former being indicative of no air bubble or particle being present in the liquid stream and the latter being indicative of the presence of an air bubble or a particle in the liquid.

In a preferred embodiment of the invention the signal produced by the detector is separated into two components, one being the steady-state DC and the other being the transient AC. The two signal components are applied to an analog to digital converter whose output is supplied to a microprocessor which uses the digital data that corresponds to the presence of the varying transient component to indicate the presence of an air bubble and/or a particle and to measure characteristics of the air bubble and/or particle. The presence of the steady-state component indicates that the system is operating properly thereby providing a continuous self check against any system malfunction.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
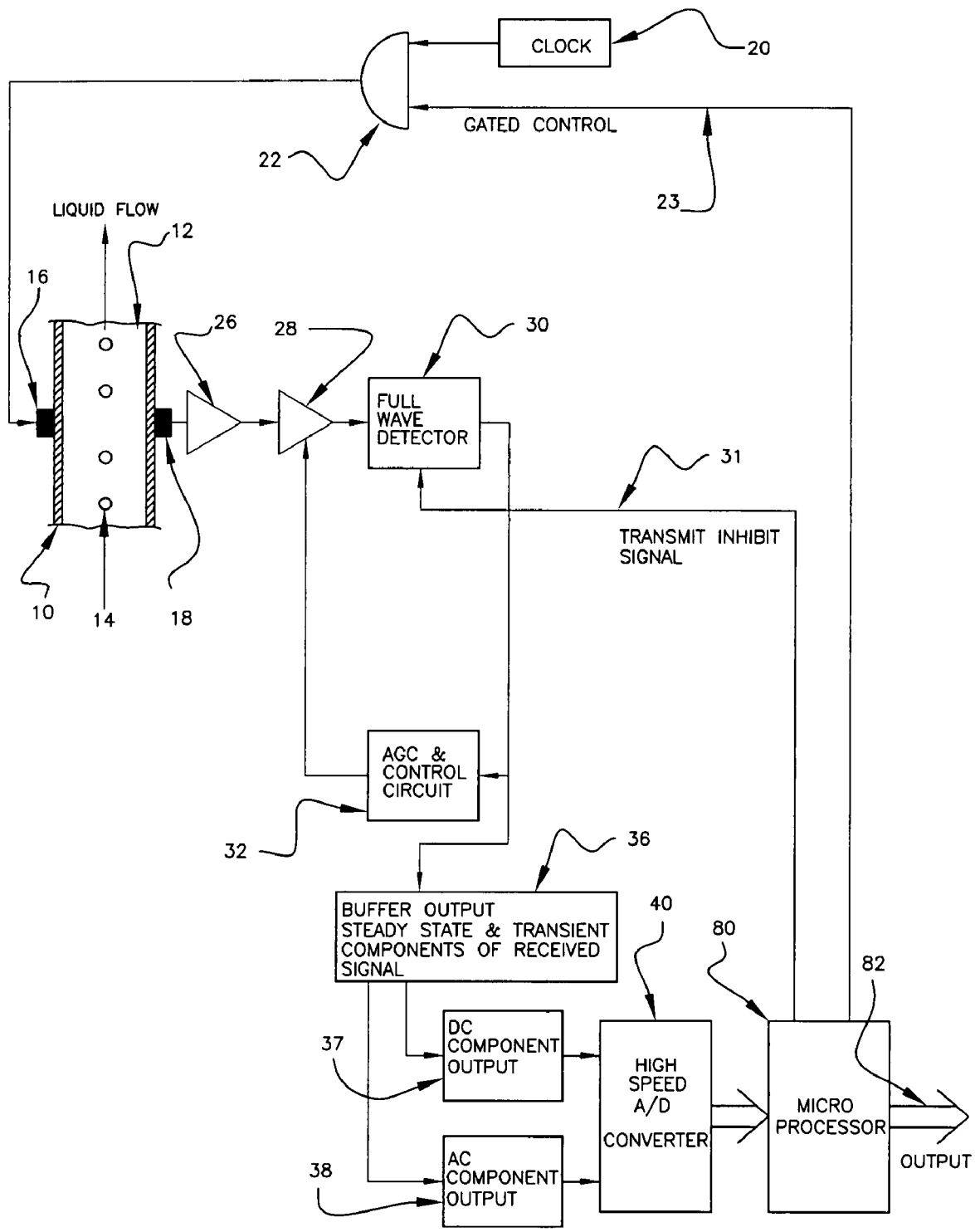
FIG. 1 is a block diagram of the system of the invention.

FIG. 1 shows a tube 10 in which a liquid 12 is flowing. The liquid 12 can be, for example, water, oil, hydraulic fluid, blood or saline. A plurality of air bubbles or particles 14 are shown in the liquid stream 12. An ultrasonic sensor formed by a pair of piezoelectric elements 16 and 18 is mounted diametrically opposed on opposites sides of the outer wall of the tube 10. The transmitter element 16 producers a relatively narrow beam of the ultrasonic energy in the height, or length, dimension of the tube 10. The sensor elements 16 and 18 can be affixed against the outer surface of tube 10 in which the liquid 12 is flowing by any suitable mechanical arrangement either individually or both elements can be in a housing that is clamped around the tube. In a preferred embodiment of the invention, the elements are mounted against the tube outer wall without using an ultrasonic conductive compound between the elements and the tube wall outer surface.

In a practical application of the invention, the tube 10 is metal or glass rigid tubing or plastic rigid or flexible tubing ranging from $\frac{1}{16}$" (1.6 mm) to $\frac{1}{12}$" (1.2 mm) inner diameter. The outer diameter of the tube is set by the type of material used and other factors. As seen, the elements 16 and 18 of the ultrasonic sensor do not come in contact with liquid flowing in the tube. This provides contamination free operation in operation since there is no contact with the liquid.

The piezoelectric transmitter element 16 on one side of the tube 10 receives ultrasonic energy of a known frequency, for example from 1 mhz to 10 mhz, provided by a clock type circuit 20 through an AND gate 22. The energy can be supplied to the transmitter element 16, either in a continuous or burst mode as controlled by a microprocessor 80. The microprocessor 80 provides a gating signal on line 23 to the AND gate 22. When the AND gate is turned on by the signal online 23 the ultrasonic energy is transmitted by the transmitter element 16 through the tube 10 and the liquid 12 flowing in it to be received by the piezoelectric receiver element 18 which converts the received ultrasonic energy to an electrical voltage signal. All of this is well known in the art.

The output signal of the sensor receiver element 18 is applied to the input an amplifier 26 which preferably is the type that can handle high frequency signals, such as an RF amplifier. The output of amplifier 26 is applied to the input of a gain controlled amplifier 28. The output of amplifier 28 is applied to the input of a detector circuit 30, preferably of the full wave type. A full wave detector is preferred because the transient signal varies both in a positive and a negative direction depending upon the type of bubble and/or particle and the ultrasonic energy also varies plus and minus. The detector circuit 30 is keyed off by a signal from the microprocessor 80 over line 31 during the time that the AND gate 22 is keyed open to provide ultrasonic energy to the sensor transmitter element 16. A portion of the detector 30 output signal is fed back to gain amplifier 28 through an AGC (Automatic Gain Control) circuit 32. This keeps the gain of amplifier 28 constant.

Figure 2:
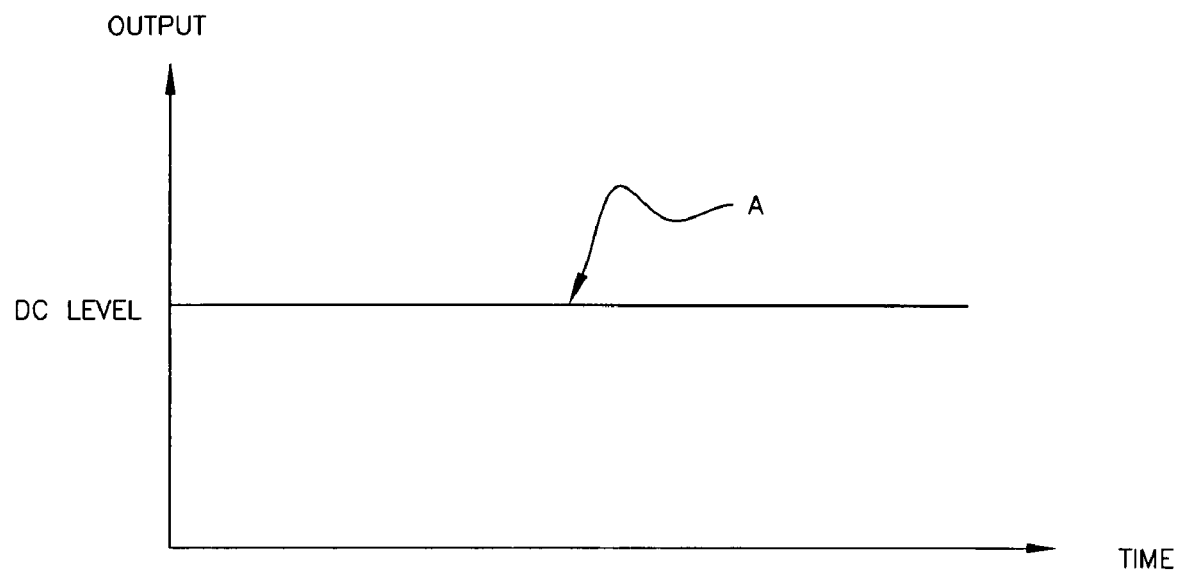
FIG. 2 shows the signal output of the sensor receiver element in a liquid flowing through the tube without any air bubble or particle being present in the liquid.
Figure 3:
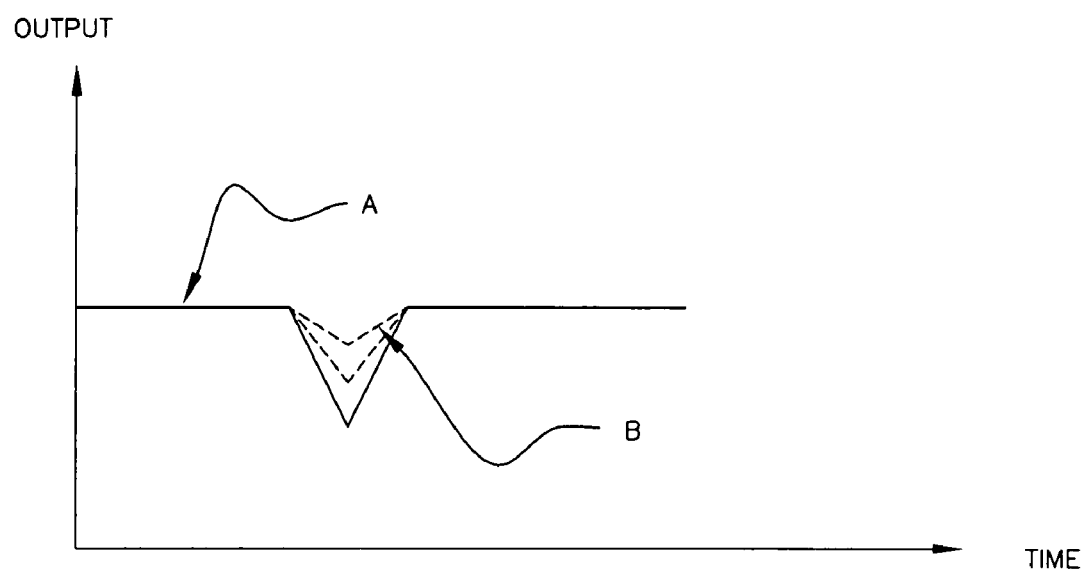
FIG. 3 shows the sensor signal output with a transient disturbance caused by the presence of an air bubble or particle in the liquid flowing in the tube.

Considering the case when there is no air bubble or particle 14 in the liquid 12 flowing in the tube 10 in the area in which the ultrasonic energy is transmitted through the liquid by the transmitter element 16, the output of the detector 30 will be a steady-state or DC signal. This is shown by line A in FIG. 2. FIG. 3 shows the voltage at the output of the detector 30 having both a DC component (line A) and an AC component B representing both steady state and transient conditions of the liquid 12 flowing through the tube 10. A transient condition occurs when an air bubble or particle passes through the ultrasonic energy path between the transmitter and receiver elements 16 and 18.

Figure 4:
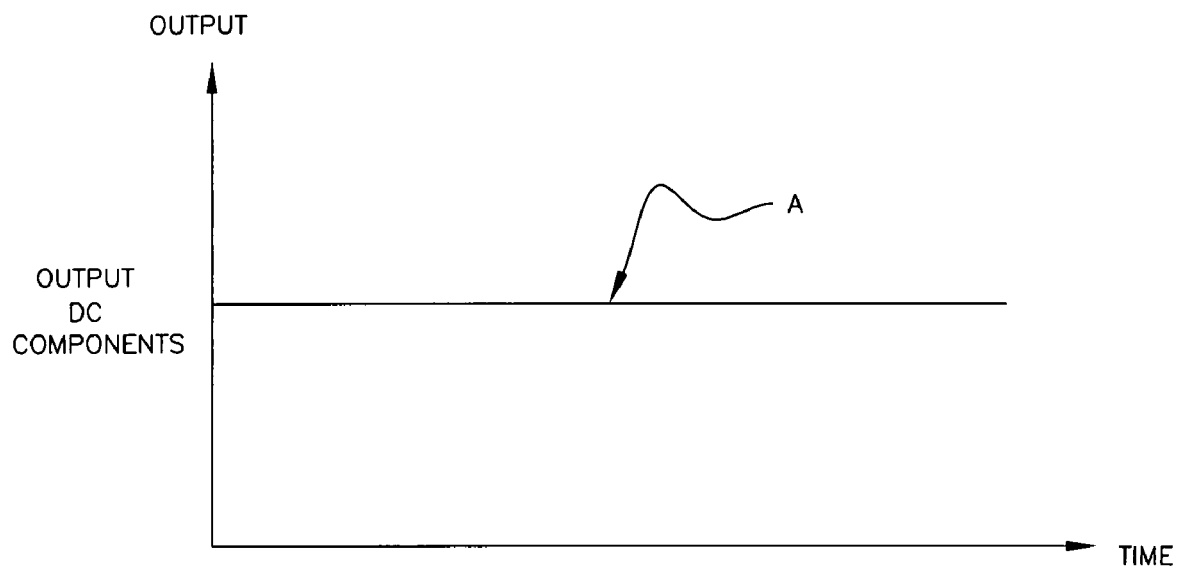
FIG. 4 shows the steady state (DC) component of the detected signal.
Figure 5:
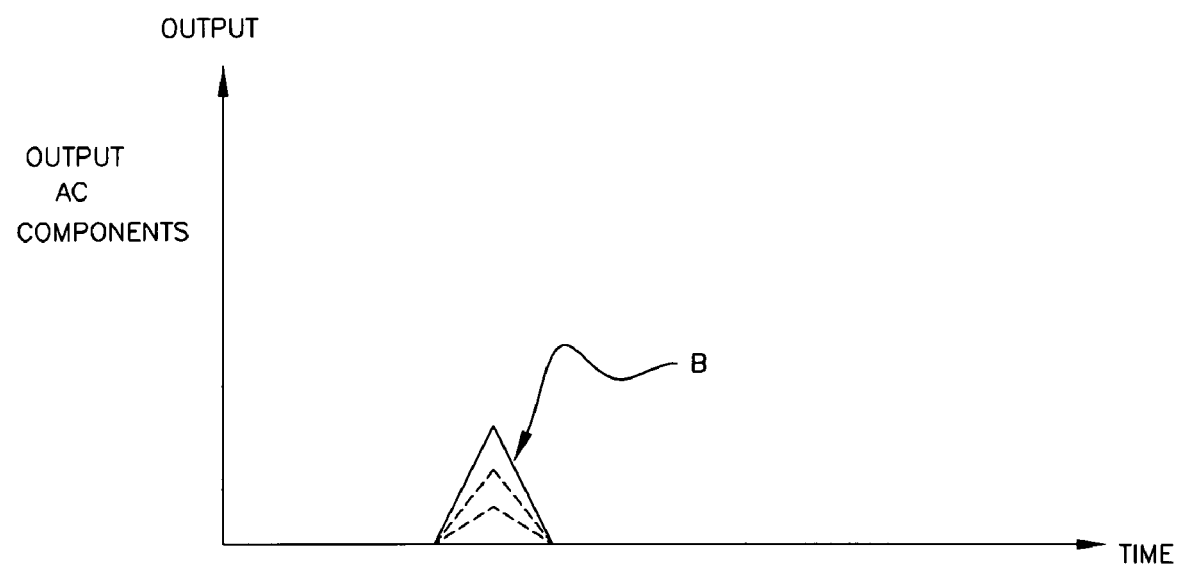
FIG. 5 shows the transient or AC component of the detected signal caused by the presence of an air bubble or particle in the liquid flowing in the tube.

In a preferred embodiment of the invention the output of the detector circuit 30, such as shown in FIG. 3, is supplied to a conditioning circuit 36 which splits the signal at the output of the detector 30 into two separate components, one being the steady-state DC component A, as shown in FIG. 4, and the other being the transient component B, as shown in FIG. 5. The conditioning produces a buffer output for the DC component of the signal received from the detector 30. It includes a DC component subtracting amplifier to null the DC component close to a zero value and pass only the AC component which is amplified by another amplifier. This is done to make the AC component have a full scale value for conversion to a digital value by an analog to digital (A/D) converter, as described below. This permits use of a less sophisticated A/D converter such as of the 8 to 10 bit type.

The output of the conditioner circuit 36 being the original signal split into its DC and AC components is supplied to the respective buffer circuits 37 and 38. The presence of the steady-state signal at the output of the buffer circuit 37 is representative of total system performance and provides a continuous self check. That is, if any electronic component of the system, such as the amplifiers 26 or 28, detector 30 or condition circuit 36, fails, or one or both of the piezoelectric transmitter and receiver elements 16 and 18 disbond, the output of the buffer circuit 37 will be zero indicative of a failure condition.

it is possible to operate the system without using conditioning circuit 36 that splits the signal into the two components. However, this requires a more sophisticated, and therefore more expensive analog to digital converter and microprocessor. Operating the system without splitting the signal into its components can still provide a continuous self check of system operation, but will require a higher precision A/D converter, such as of the more expensive 12-16 bit type to characterize the bubble or particle size since the full scale input of the A/D converter becomes a limitation. For example, if the A/D converter has a 2 volt full scale input limitation then the DC component will take 50% leaving only 50% for the AC component, thereby limiting the characterization of the bubble or particle.

The outputs of the buffer circuits 37 and 38 are supplied to the input of a high-speed analog to digital (A/D) converter 40. The A/D converter 40 can be a separate component or can be part of the microprocessor 80. The A/D converter 40 operates on a continuous basis relative to the signal components that it receives, for example, sampling every 10 microseconds, and supplies digital data to the microprocessor 80 for indicating the presence of and for analyzing and quantifying the size of an air bubble or particle. The microprocessor 80 has an output 82 which can be provided to any suitable type of a display for viewing by an operator of the system In operation of the system, when an air bubble or particle 14 passes through the ultrasonic energy path established by the transmitter element 16, the standing wave envelope will be disturbed to produce a different standing wave pattern. The amplitude of a signal received by the sensor receiving element 18 decreases as changes occur in the phase shift and acoustic attenuation as the ultrasonic energy is generated in the liquid flowing in the tube 10. That is, the presence of an air bubble or particle will interfere with the ultrasonic energy produced by the transmission and reception of ultrasonic mechanical energy across the tube carrying liquid. An air bubble and/or particle will block a portion of the mechanical energy depending upon the volume/diameter of the air bubble and/or particle and amount of mechanical block. The change in the amplitude of the received signal caused by perturbations due to an air bubble and/or particle 14 present in the liquid 12 is detected by the high-frequency amplifier 26, gain controlled amplifier 28, and detector circuit 30.

Microprocessor 80 acts like a pulse height analyzer as it receives the digital data from the high speed A/D converter 40. The amplitude height change of the transient signal relative to the steady-state detected by the microprocessor by the sampling of the signal component received from the buffer circuit 38 reflects the size of an air bubble and/or particle. The microprocessor 80 also is programmed to operate to measure the duration of the transient signal and its change in amplitude over time thereby quantifying the volume or diameter of the air bubbles and/or particles. That is, different size air bubbles and particles produce different transient signal amplitude due to their relative cross sectional area. A particle and/or air bubble having a size greater than $\lambda/3$ ($\lambda$: wave length) of the frequency of the ultrasonic energy supplied to the sensor transmitter element 16 can be detected fairly reliably by the system of the invention.

The microprocessor 80 also can be programmed to count the number of air bubbles and/or particles that are flowing in the liquid stream and this can be done on a per unit of time basis. The total volume of air bubbles also can be computed, this being useful in some types of medical procedures.

The system of the invention has numerous advantages. These include: continuous in-line monitoring, flow rate independency and the ability to handle all fluids including opaque liquids. Another advantage is the elimination of contamination associated with an invasive sensor, that is, one that has an element that comes into contact with the liquid. The system is useful for various medical application in which accumulated air volume has to be precisely calculated. In a typical application where the liquid is water, blood or saline solution, using ultrasonic energy and a frequency of 10 mhz where an ultrasonic wavelength is about 0.15 mm the system can detect air bubbles and/or particle size from 0.075 mm diameter and larger.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. A system for detecting the presence of an air bubble and/or particle in a liquid flowing in a tube, comprising:
    an ultrasonic sensor of a transmitter element and a receiver element mounted on the outside of the tube opposing each other;
    a generator of ultrasonic energy supplied to said transmitter element and transmitted through a liquid flowing in the tube to be received by said receiver element and be converted into an electrical signal at an output of said receiver element;

a conditioning circuit which splits said electrical signal into a steady-state component corresponding to there being no air bubble and/or particle in the liquid and a transient state component corresponding to an air bubble and/or particle being present;

an analog to digital converter to convert the steady state and transient signal components from the output of said conditioning circuit into digital data; and a microprocessor responsive to the digital data to detect the presence of an air bubble and/or particle in the liquid.

2. The system as claimed in claim 1 wherein said microprocessor operates to detect the failure of the system in response to the absence of the steady state component.

3. The system as claimed in claim 2 wherein said microprocessor also operates to determine the characteristics of an air bubble or particle based on the characteristics of the transient component.

4. The system as claimed in claim 1 wherein said microprocessor operates to determines the characteristics of an air bubble or particle based on the characteristics of the transient component.

5. A system for detecting the presence of an air bubble and/or particle in a liquid flowing in a tube, comprising:

an ultrasonic sensor of a transmitter element and a receiver element mounted on the outside of the tube opposing each other;

a generator of ultrasonic energy supplied to said transmitter element and transmitted through a liquid flowing in the tube to be received by said receiver element and be converted into an electrical signal at an output of said receiver element;

a conditioning circuit which splits said electrical signal into a steady-state component corresponding to there being no air bubble and/or particle in the liquid and a transient state component corresponding to an air bubble and/or particle being present;

an amplifier for amplifying the electrical signal from said sensor receiver element that is applied to said conditioning circuit;

a detector circuit that receives the signal from the output of said amplifier, the output of said detector circuit being applied to said conditioning circuit;

an analog to digital converter to convert the steady state and transient signal components from the output of said conditioning circuit into digital data; and a microprocessor responsive to the digital data to detect the presence of an air bubble and/or particle in the liquid.

6. The system as claimed in claim 5 wherein said microprocessor operates to detect the failure of the system in response to the absence of the steady state component signal.

7. The system a claimed in claim 5 wherein said detector is a full wave detector.

8. The system as claimed in claim 7 wherein said microprocessor operates to detect the failure of the system in response to the absence of the steady state component signal.

9. The system as claimed in claim 7 wherein said microprocessor operates to determines the characteristics of an air bubble or particle based on the characteristics of the transient component signal.

10. The system as claimed in claim 5 wherein said microprocessor operates to determines the characteristics of an air bubble or particle based on the characteristics of transient component signal.

\* \* \* \* \*